US012667406B2

(12) United States Patent
Murdeshwar et al.

(10) Patent No.: US 12,667,406 B2
(45) Date of Patent: Jun. 30, 2026

(54) DEVICE FOR TREATING ENDOMETRIOSIS

(71) Applicant: GYRUS ACMI, INC., Southborough, MA (US)

(72) Inventors: Nikhil M. Murdeshwar, Maple Grove, MN (US); Thomas J. Holman, Princeton, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 544 days.

(21) Appl. No.: 17/096,061

(22) Filed: Nov. 12, 2020

(65) Prior Publication Data

US 2021/0153922 A1      May 27, 2021

Related U.S. Application Data

(60) Provisional application No. 62/939,779, filed on Nov. 25, 2019.

(51) Int. Cl.
| | |
|---|---|
| *A61B 18/04* | (2006.01) |
| *A61B 18/00* | (2006.01) |
| *A61B 18/14* | (2006.01) |

(52) U.S. Cl.
CPC ............ *A61B 18/042* (2013.01); *A61B 18/14* (2013.01); *A61B 2018/00065* (2013.01);
(Continued)

(58) Field of Classification Search
CPC ........ A61B 18/042; A61B 2018/00065; A61B 18/14; A61B 2018/00559;
(Continued)

(56) References Cited

U.S. PATENT DOCUMENTS

| | | | | |
|---|---|---|---|---|
| 5,207,675 A | * | 5/1993 | Canady .............. | A61B 18/1482 606/49 |
| 6,391,027 B1 | * | 5/2002 | Farin ..................... | A61B 18/14 606/45 |

(Continued)

FOREIGN PATENT DOCUMENTS

| | | |
|---|---|---|
| CN | 112826588 A | 5/2021 |
| EP | 0604539 A1 | 7/1994 |

(Continued)

OTHER PUBLICATIONS

"European Application Serial No. 20209751.5, Extended European Search Report mailed Apr. 21, 2021", 11 pgs.

(Continued)

*Primary Examiner* — Adam Z Minchella
*Assistant Examiner* — Ashleigh Lauren Kern
(74) *Attorney, Agent, or Firm* — Schwegman Lundberg & Woessner, P.A.

(57) ABSTRACT

An electrotherapeutic device can be configured for at least partial insertion into a patient. The device can include a shaft including a proximal portion and a distal portion, a gas-delivery lumen extending between the proximal portion and the distal portion of the shaft, and one or more electrodes located near the distal portion of the shaft. The electrodes can include a plasma activation electrode for generating plasma from gas delivered to the distal portion of the shaft via the gas-delivery lumen, and an ablation electrode for generating electromagnetic ablation energy. The medical device can be used in a method of treating endometriosis including delivering a gas toward an in vivo treatment site within a patient, generating plasma from the gas on or near the in vivo treatment site using a plasma activation electrode, exposing the treatment site to the plasma, and apply- (Continued)

ing electromagnetic ablation energy to treat endometrial tissue.

17 Claims, 4 Drawing Sheets

(52) U.S. Cl.
CPC ............... *A61B 2018/00559* (2013.01); *A61B 2018/00577* (2013.01); *A61B 2018/00601* (2013.01); *A61B 2018/1412* (2013.01)

(58) Field of Classification Search
CPC ........... A61B 2018/00577; A61B 2018/00601; A61B 2018/1412; A61B 2017/00367; A61B 2017/00393; A61B 18/12; A61B 18/1485; A61B 18/04; A61B 18/18; A61B 2018/00583
See application file for complete search history.

(56) References Cited

U.S. PATENT DOCUMENTS

| | | | | |
|---|---|---|---|---|
| 2002/0022838 A1* | 2/2002 | Cunningham | ....... | A61B 18/042 |
| | | | | 606/49 |
| 2003/0084907 A1 | 5/2003 | Pacek et al. | | |
| 2003/0181904 A1* | 9/2003 | Levine | ............... | A61B 18/1402 |
| | | | | 606/49 |
| 2005/0010205 A1* | 1/2005 | Hovda | ............... | A61B 18/1482 |
| | | | | 606/41 |
| 2006/0264928 A1* | 11/2006 | Kornerup | ........... | A61B 18/1402 |
| | | | | 606/49 |
| 2008/0167645 A1 | 7/2008 | Woloszko | | |
| 2010/0114092 A1* | 5/2010 | Eisele | .................. | A61B 18/042 |
| | | | | 606/41 |
| 2011/0077646 A1* | 3/2011 | Dahla | ............... | A61B 18/1402 |
| | | | | 606/41 |
| 2013/0237982 A1* | 9/2013 | Rencher | ................. | A61B 18/10 |
| | | | | 606/45 |
| 2013/0345670 A1* | 12/2013 | Rajagopalan | ........ | A61B 18/042 |
| | | | | 606/1 |
| 2013/0345705 A1* | 12/2013 | Truckai | .................. | A61B 18/14 |
| | | | | 606/49 |
| 2014/0039489 A1* | 2/2014 | Davalos | ............. | A61B 18/1206 |
| | | | | 606/41 |

FOREIGN PATENT DOCUMENTS

| | | | |
|---|---|---|---|
| EP | | 2996768 A1 | 3/2016 |
| EP | | 3360492 A1 | 8/2018 |
| WO | WO-2011060189 A1 | | 5/2011 |

OTHER PUBLICATIONS

"European Application Serial No. 20209751.5, Response Filed to Nov. 17, 2021 Extended European Search Report mailed Apr. 21, 2021", 7 pgs.

* cited by examiner

300

DEVICE FOR TREATING ENDOMETRIOSIS

CROSS-REFERENCE TO RELATED APPLICATION

This application claims the benefit of priority to U.S. Provisional Patent Application Ser. No. 62/939,779 filed Nov. 25, 2019, the contents of which are incorporated herein in their entirety.

BACKGROUND

Endometriosis is a condition in which tissue that normally lines the inside of the uterus, the endometrium, grows outside the uterus. Endometriosis can cause severe, ongoing chronic pain. Often, endometriosis occurs in and around the pelvis, such as near the ovaries, fallopian tubes, and other tissue lining the pelvis. In rare cases, endometrial tissue can spread beyond pelvic organs. Endometriosis can include shallow endometrial tissue growth in and around these areas, deeper endometrial tissue growth, or both.

SUMMARY/OVERVIEW

A variety of approaches can be taken for treatment of endometriosis. For example, radiofrequency (RF) ablation is an approach that can use an electrode providing electromagnetic energy for ablation tissue or that can provide a blade-like device for physically excising tissue. Gas plasma is an approach that can be used for shallow ablation of tissue sites. Some approaches can involve multiple treatments and procedures, which, in turn, can limit efficacy or introduce complications.

To help increase efficacy and reduce complications, the present disclosure describes, among other things, an integrated approach to electromagnetic ablation and gas plasma treatment of endometriosis.

Such an approach can include providing or using an electrotherapeutic device for at least partial insertion into a patient. The device can include a shaft, which can include a proximal portion and a distal portion. A gas-delivery lumen can extend between the proximal portion and the distal portion of the shaft. One or more electrodes can be located at or near the distal portion of the shaft. The one or more electrodes can include at least one plasma activation electrode, such as can be configured to be actuatable, such as for generating plasma from gas that can be delivered to the distal portion of the shaft, such as via the gas-delivery lumen. The one or more electrodes can include at least one electromagnetic ablation electrode, such as can be configured to be actuatable, such as for generating electromagnetic ablation energy.

Such an approach can include a method of treating endometriosis. The method can include delivering a gas toward an in vivo treatment site within a patient, generating plasma from the gas on or near the in vivo treatment site using a plasma activation electrode, exposing the treatment site to the plasma to treat endometrial tissue, and applying electromagnetic ablation energy to treat endometrial tissue.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

DETAILED DESCRIPTION

Figures 1A, 1B:
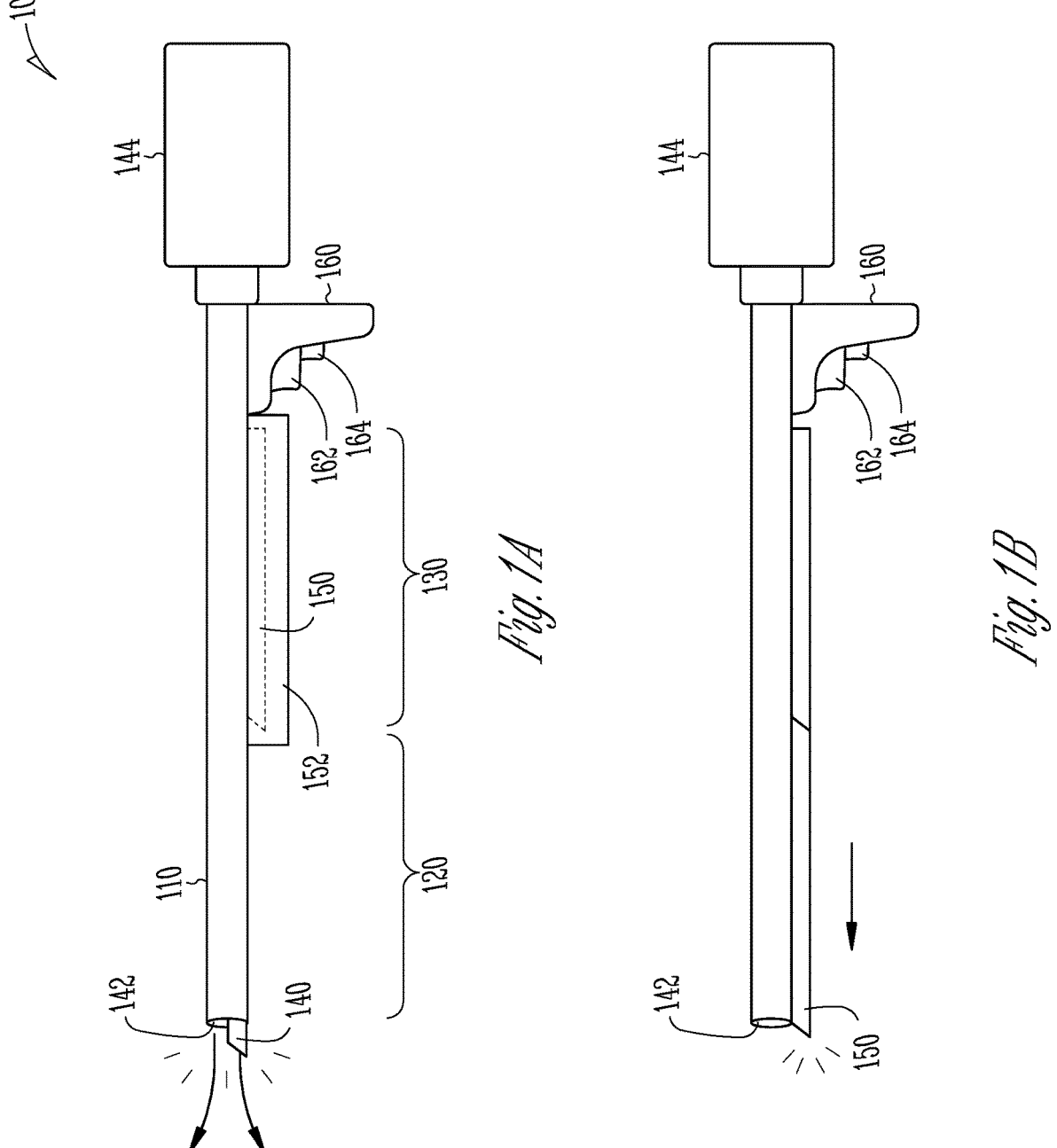
FIGS. 1A-1B illustrate schematic diagrams of an example of a device that can be used for treating endometriosis.

The present disclosure describes, among other things, devices and methods that can be used to treat a patient, such as for locally treating endometriosis in which both shallow and deep endometrial tissue build-up has occurred outside the uterine wall.

For example, an electrosurgical ablation device can include both an electrode for producing RF or other electromagnetic ablation energy and an electrode to induce plasma formation at a treatment site. In some cases, one electrode can be used to both ionize gas to produce gas plasma, and to oscillate current and produce RF energy for ablation. As explained further herein, deep endometrial lesions can be excised or ablated with mono- or bi-polar RF or another electromagnetic ablation energy. Shallow sites of endometrial tissues, by comparison, can be ablated with gas plasma (such as argon or carbon dioxide gas plasma), such as without requiring removal and re-insertion of the device during the interventional procedure.

Gas plasma has minimal tissue penetration. For this reason, gas plasma treatment can be useful in a situation in which the area being treated is nearby thin tissue or in sensitive areas such as a bowel, bladder, or near nerves. In general, this disclosure may use the terms "plasma," "conductive gas" and "ionized gas" interchangeably. A plasma includes of a state of matter in which electrons in a neutral gas are stripped or "ionized" from their molecules or atoms. Such plasmas can be formed by application of an electric field or by high temperatures. In a neutral gas, electrical conductivity is non-existent or very low. Neutral gases act as a dielectric or insulator until the electric field reaches a breakdown value, freeing the electrons from the atoms in an avalanche process thus forming a plasma. Such a plasma provides mobile electrons and positive ions, and acts as a conductor which supports electric currents and can form spark or arc. Due to their lower mass, the electrons in a plasma accelerate more quickly in response to an electric field than the heavier positive ions, and hence carry the bulk of the current.

Electromagnetic energy, such as radiofrequency (RF) energy, can be used for deeper tissue ablation. In general, electromagnetic energy can include the waves (or their quanta, photons) of the electromagnetic field, propagating through space carrying electromagnetic radiant energy. These can include radio waves, microwaves, infrared light, visible light, ultraviolet light, x-rays, and gamma rays.

Both electromagnetic (e.g., RF) ablation and gas plasma ablation, can be used or tailored to surgically treat diseased endometrial tissue. A device incorporating multiple options, such as both for treatment of deep endometrial lesions (e.g., via RF or other electromagnetic ablation) and shallow endometrial tissue build-up (e.g., via gas plasma ablation), can help provide flexibility in treatment during a particular procedure, such as with a single, self-contained interventional device portion, such as without requiring removal and re-insertion, which can affect efficacy and cost.

Ablation can include, for example, any type of tissue effect produced by radiofrequency ablation, gas plasma ablation, or other types of electromagnetic energy, that causes removal of endometrial tissue. Ablation can be done, for example, by direct or indirect contact between the target tissue and one or more electrodes. Ablation can be done, for example, with or without direct electrical contact between the target tissue and the one or more electrodes. In some cases, the electrodes can produce electromagnetic energy for ablation that is converted to a different portion of the spectrum. For example, radiofrequency energy associated with an electrode could be converted to infrared, ultraviolet, or other type of electromagnetic frequencies, to result in a desired degree of ablation.

FIGS. 1A-1B are schematic diagrams illustrating examples of portions of a device 100 such as can be used for treating endometriosis. The device 100 can be, for example, part of an electrosurgical ablation system such as for treatment of endometriosis. In FIG. 1A, the device 100 is shown in a plasma ablation configuration or mode. In FIG. 1B, the device 100 is shown in an electromagnetic energy ablation configuration or mode. FIGS. 1A-1B will be discussed together.

The device 100 can include an elongated shaft 110 with a distal portion 120 and a proximal portion 130, a first electrode 140, a gas-delivery lumen 142 coupled with a gas source 144, a second electrode 150, and a handle 160, such as with a first trigger 162 and a second trigger 164.

The device 100 can include one or more portions, such as the shaft 110, that can be sized, shaped, arranged, or otherwise configured to allow insertion into a patient, such as through an incision in the abdomen or via a transcervical route into the uterus. The device 100 can include a hand piece, such as the handle 160, connected to the proximal portion 130 of the shaft 110. The handle 160 can remain external to the patient and accessible to the physician or other user when the shaft 110 is inserted into the patient. A gas source 144 can be fluidly connected to the gas-delivery lumen 142, such as to carry gas from the handle 160 to the distal portion 120 of the shaft such as for plasma generation when the distal portion 120 of the shaft 110 is located in vivo within the uterus. For example, the gas source 144 can include a gas canister that can be mounted in or on the handle 160. The gas delivery lumen 142 can be defined and can extend longitudinally with the shaft 110, or it can be a separate tube that can longitudinally extend external to the shaft 110, such as by using a tube that can be attached to the shaft 110.

Both the first electrode 140 and the second electrode 150 can be located at or near a distal portion 120 of the shaft 110, such as at or near the distal end. The first electrode 140 and the second electrode 150 can be mechanically attached to or integral with the shaft 110. In some cases, the first electrode 140 and the second electrode 150 can be electrically insulated from the shaft. In other cases, the first electrode 140 or the second electrode 150, or both electrodes, can be electrically integrated with the shaft 110, such that the shaft 110 can served as a return path for electromagnetic energy from the first electrode 140, the second electrode 150, or both electrodes.

For example, the first electrode 140 and the second electrode 150 can be mounted on or in the shaft 110. For example, the first electrode 140 can be mounted in or near an outlet of the gas-delivery lumen 142 near the distal portion 120 of the shaft 110 to allow the first electrode 140 to ionize nearby gas exiting the gas-delivery lumen 142, such as at a location within the patient such as to generate plasma at an in vivo location within the patient.

The second electrode 150 can be, for example, mounted externally on the shaft 110. In some cases, the second electrode 150 can be in a user-retractable configuration, such as to allow the second electrode 150 to be retracted longitudinally along and with respect to the shaft 110. In a user-retractable configuration, the second electrode 150 can include a mode in which the second electrode 150 is retracted and is not in use for RF ablation. In a user-retractable configuration, the second electrode 150 can be user-extended longitudinally along and with respect to the shaft 110, such as in a mode in which the second electrode 150 is to be used for RF ablation. When the second electrode 150 is user-retractable, the operator can choose when to use the first electrode 140 without interference from the second electrode 150. Moreover, if the second electrode 150 has a blade or spatula configuration, retracting the second electrode 150 along the shaft 110 for insertion can protect the patient from accidental scrapping or cutting.

In some cases, the shaft 110 can be sized, shaped, arranged, or otherwise configured for laparoscopy, in other cases, shaft 110 can be shorter such as for open surgery applications. Laparoscopy can include, for example, a surgical procedure in which a small incision is made, through which a device is inserted to diagnose or treat conditions. Laparoscopy is considered less invasive than regular open abdominal surgery. In the case of laparoscopy, an optical device may also be inserted with device 100, where the optical device allows imaging for the operator to observe the tissue. The optical device can include, for example, a laparoscope, or viewing tube, with a camera. In other cases, the operator could use an ultrasound type imaging device during treatment. Laparoscopy or open surgery can be used where endometriosis is occurring substantially outside the uterus.

For example, in a laparoscopy application, the shaft 110 can have a length in a range of 10 mm to 30 mm, inclusive. The shaft 110 can be narrow in a cross-section or a lateral dimension, such as for patient insertion via a cervical opening or via an incision. For example, the shaft 110 can have a cross-sectional or lateral width in a range of less than 5 mm, inclusive. The shaft 110 can include or can be made of one or more of a composite, plastic, or metallic material, or other material suitable for gynecology ablation medical devices.

The proximal portion 130 of the shaft 110 can be anchored to handle 160 such as by mechanical fasteners or adhesive. The handle 160 can be sized, shaped, arranged or otherwise configured as a hand piece for a physician or other user to hold and direct insertion of the shaft 110 into the patient or other movement and operation of the device 100. The handle 160 can include one or more user-actuators, such as the user-actuatable first and second triggers 162, 164. The first trigger 162 can provide a user-interface to control a first switch that selectively connects the first electrode 140 to an energy source or circuitry that can provide electrical energy to the first electrode 140 such as for initiating or sustaining plasma generation within the patient. The second trigger 164 can provide a user-interface to control a second switch that selectively connects the second electrode 150 to an energy source or circuitry that can provide electrical energy to the second electrode 150 such as for initiating or sustaining RF or other electromagnetic ablation within the patient. The handle 160 can include or can be communicatively coupled to one or more alternative or additional buttons, triggers, or controls, such as to allow the user to actuate energy delivery to the first electrode 140, the second electrode 150, or other portion or component of device 100, such as a corresponding longitudinal extension/retraction translation mechanism upon which an individual one of the electrodes 140, 150 rides.

In the example of FIGS. 1A and 1B, the first trigger 162 can actuate the first electrode 140, such as to induce plasma formation, such for gas plasma ablation as discussed herein. The second trigger 164 can actuate the second electrode 150, such as for electromagnetic energy ablation that need not involve plasma generation, as discussed herein. In other examples, one or more foot pedals connected to the device 100 can be used to actuate the device 100, such as foot pedals connected by wiring to the device 100.

The first and second electrodes 140, 150 can be mounted in or on the shaft 110 of device 100. The first and second electrodes 140, 150, can be configured to be respectively actuatable by the user individually or concurrently to respectively produce plasma ablation and/or electromagnetic ablation not requiring plasma generation. In FIGS. 1A and 1B, the first and second electrodes 140, 150, are shown as separate electrodes, such as in which the first electrode 140 can be configured to spark plasma generation at a location within the patient, and the second electrode 150 can be configured to produce electromagnetic energy for ablation not requiring plasma. As shown and discussed in reference to FIG. 2 below, a single electrode (240) can potentially function in both plasma and non-plasma ablation capacities.

The first and second electrodes 140, 150 can respectively be switchable connected via respective electrical conductors to an electromagnetic energy source, such as to electrosurgical generator (ESG) circuitry configured to provide suitable RF or other electromagnetic ablation energy or plasma generation energy. The ESG circuitry can include appropriate power conversion circuitry and can, in turn, be connected to an electrical power source such as a wall plug or one or more batteries supplying energy.

The first electrode 140 can include a plasma activation electrode configured ionize gas and induce plasma generation in vivo. First electrode 140 can be at or near a distal portion 120 of shaft 110, such as at or near an outlet to gas-delivery lumen 142.

Shown in FIG. 1A, when the device 100 can be activated for plasma generation, a gas can exit the gas-delivery lumen 142 near the distal portion 120 of the shaft 110. The end of the distal portion 120 of the shaft 110 can be positioned so that it can be nearby the desired treatment site, such as a site having shallow endometrial lesions.

Gas flow down the gas-delivery lumen 142 can be controlled through the use of a pump, one or more valves, or additional buttons, triggers, or other activation switches on or connected to the device 100 or the handle 160. In some cases, the gas flow down the gas-delivery lumen 142 can be actuatable directly from the gas source 144, such as by a valve or actuator at an outlet of the gas source 144. In other cases, the flow of gas down gas-delivery lumen 142 can be triggered by the same trigger associated with activated of the first electrode 140 and gas plasma generation.

The first electrode 140 and the second electrode 150 can be, for example, bipolar or monopolar electrodes. Both bipolar and monopolar electrodes can make use of high frequency electrical current to cut, coagulate, desiccate, or fulgurate tissue. With a monopolar electrode, the current can pass from the probe of the electrode to the target tissue and through the patient to a return pad attached elsewhere on the patient to complete the electrical circuit. In contrast, with a bipolar electrode, current passes through the tissue between two arms of a forceps-type electrode. For this reason, bipolar electrodes offer a shorter electrical pathway.

The first electrode 140 can be energized to ionize the gas being discharged, such as by engaging the first trigger 162, to provide electrical energy to the first electrode 140 to generate in vivo a spark or other plasma-generating energy. The ignition can cause an arc to be struck between the grounded treatment site and the first electrode 140, generating plasma from the gas exiting gas-delivery lumen 142. For application of gas plasma, the treatment site tissue can be grounded to provide a return path for electricity when the arc is struck. The tissue can be grounded by a separate pad attached to the tissue, or by a prong of the electrode itself. In the case of a monopolar electrode, the arc can be struck between the electrode and a return pad on the patient. In the case of a bipolar electrode, the arc can be struck between the two sides (e.g., forceps) of the electrode. The first electrode 140 can be activated and strike and arc to generate plasma at a constant rate, or in a pulsatile rate, depending on the desired treatment site tissue.

The electromagnetic energy travelling over the arc can generate plasma where it interacts with the gas by ionizing that gas to produce plasma. Where plasma, which is in effect a highly ionized gas, touches the treatment site, the tissue can be ablated by the damage done by the ionized gas, disrupting tissue structure resulting in scarred tissue that may no longer act like uterine lining and cycle throughout the month. The treated tissue can have higher electrical impedance compared to untreated tissue. The plasma can spread toward and along the anatomical surface of the treatment site, seeking low impedance tissue areas (that is, untreated tissue). When the first electrode 140 creates an arc, the arc can vaporize tissue and result in small fissures in the tissue created by sparks, which can allow for deeper tissue destruction as current flows along a tissue's path of least resistance (e.g., untreated tissue), this can sometimes cause vessels that may go on to bleed. These vessels can be coagulated, for example, by application of an RE electrode such as the second electrode 150.

FIGS. 1C-1F illustrate schematic diagrams of examples of configurations of the electrodes 140, 150 such as can be used for generation of plasma and treating endometriosis.

Figure 1C:
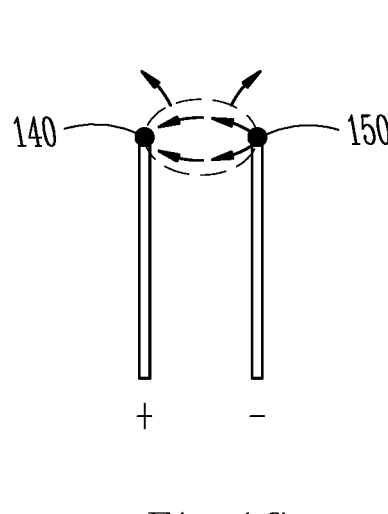
FIGS. 1C-1F illustrate schematic diagrams of examples of electrodes for use in an example of a device that can be used for treating endometriosis.

FIG. 1C illustrates an example of a bipolar electrode configuration of closely-spaced electrode electrodes 140, 150. Each of the electrodes 140, 150, can be located at or near the end of the distal portion 120 of the shaft 110, such as, for example at opposing sides of an outlet of the gas-delivery lumen 142. In some examples, the electrodes 140, 150, can be downstream of the gas-delivery lumen 142 such that gas exiting the gas-delivery lumen 142 passes over the electrode 140, 150.

Respective individual conductors can extend proximally from the electrodes 140, 150 along the shaft 110, such as toward the handle 160, at which such conductors can be connected to an electrical energy source. The first electrode 140 can be associated with a first pole, such as a positive charge, and the second electrode 150 can be associated with a second pole, such as a negative charge. The second electrode 150 can serve as a return electrode, complimenting the first electrode 140. The electrical energy source can provide an AC current to the first electrode 140, providing sufficient electromagnetic energy thereto to provide an arc or otherwise ionize the gas passing between the electrodes 140, 150.

The close spacing between the electrodes 140, 150 can allow for easier ionization of the gas passing by and can help advantageously provide directional localized treatment, such as of endometriosis. Plasma generation can be highly controlled in this configuration. For example, in this configuration of FIG. 1C, the plasma generation can be relatively less sensitive to the quantity, density, or purity of gas passing by the electrodes 140, 150. In some cases, this configuration can allow for more directional treatment of endometrial lesions, as the physical space between electrodes 140, 150, where an arc can be struck to ionize gas into plasma, can be small.

Figure 1D:
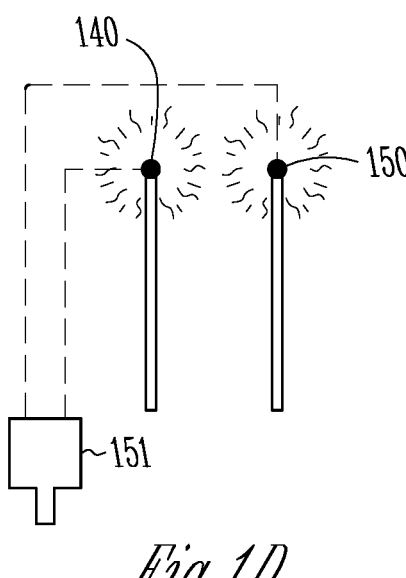

FIG. 1D illustrates an example of a monopolar electrode configuration, such as can include distal plasma generation electrodes 140, 150 and a global return pad electrode 151. The distal plasma generation electrodes 140, 150 can be located at or near the end of the distal portion 120 of the shaft 110, such as, for example at opposing sides of an outlet of the gas-delivery lumen 142. The global return pad electrode 151 can be located elsewhere on the patient, for example, on an adhesive patch that can be applied and adhesively secured to the patient's skin, and can serve as a grounding electrode. The surface area of the global return pad electrode 151 can be relatively larger than a surface area of the distal plasma generation electrodes 140, 150.

In FIG. 1D, plasma can be generated at each of the electrodes 140, 150. Both electrodes 140, 150, can spark an arc between itself and a target tissue area to ionize gas in a region between the gas discharge outlet and the target tissue. The return path electrode 151 can be electrically connected to the target tissue. This monopolar electrode configuration shown in FIG. 1D can help allow for a larger region in which gas can be ionized to produce plasma. Thus, the electrode configuration of FIG. 1B can help provide a more omnidirectional or global ablation of tissue, such as for treating a larger region of endometriosis more quickly than a more localized and directional configuration.

Figure 1E:
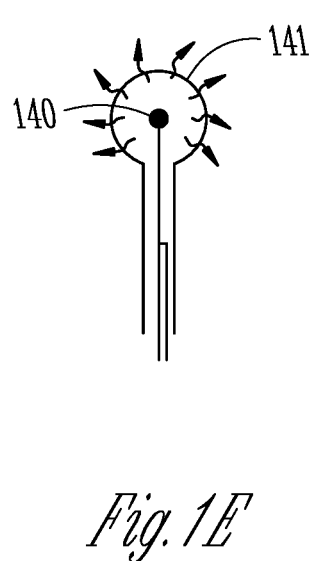

FIG. 1E illustrates an example of an ion-porous housing 141 about at least one distal electrode 140, with a return electrode provided by one or more of another bipolar distal electrode within the housing, a monopolar electrode that can be electrically coupled externally or otherwise with tissue of a patient, or by providing an electrically conductive housing electrode. The electrode 140 and ion-porous housing 141 can be located at or near the end of the distal portion 120 of the shaft 110, such as, for example at opposing sides of an outlet of the gas-delivery lumen 142.

In an example, the ion-porous housing 141 can include a glass or other dielectric bulb at least partially surrounding the electrode 140. The ion-porous housing 141 can include pores to allow gas or plasma ions, or both, to exit the housing. The electrode 140 can be energized electrically to arc to the target tissue to ionize incoming gas, or otherwise ionize gas within the bulb or other housing, such that ionized gas can exit the glass bulb or other housing near the treatment site.

Figure 1F:
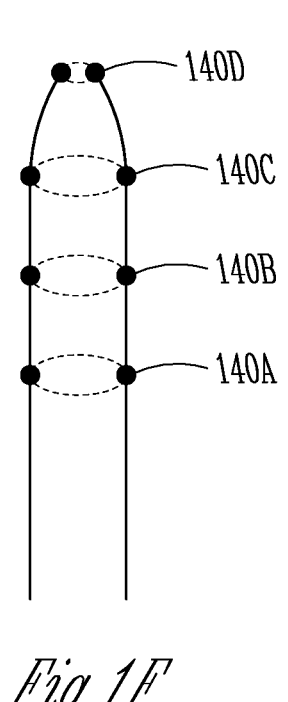

FIG. 1F illustrates an example of a plasma knife electrode configuration, such as can include a first set of plasma activation electrodes arranged in a first group 140A (e.g., on a first plane) and a second set of plasma activation electrodes arranged in a second group 140B (e.g., on a second plane) such as for forming gas plasma ions on the first and second planes, respectively, in addition to a third group 140C (e.g., on a third plane), and a fourth group 140D (e.g., on a fourth plane). The groups of electrode 140A-140D can, for example, reside in planes parallel each other. The groups of electrodes 140A-140D can be located at or near the end of the distal portion 120 of the shaft 110, such as, for example at opposing sides of an outlet of the gas-delivery lumen 142.

The plasma knife electrode configuration of FIG. 1F can help efficiently produce gas plasma ions in a planar arrangement for enhancing cutting at such geometrically planar locations. Additional or fewer groups of electrodes can be included as desired for certain cutting effects.

The gas source 144 can include, for example, a canister or other container, a hose, or other means for providing gas such as can be ionized in vivo to produce a plasma such as for ablation. The gas source 144 can be fluidly connected to the gas-delivery lumen 142 to allow gas to flow along the shaft 110 to an outlet of the gas at or near the distal portion 120 of the shaft 110, where the first electrode 140 can ignite an arc and produce plasma from the gas. For example, the gas source 144 can include one or more of carbon dioxide, argon, metal halides, other noble gases, or other types of one or more gases as desired. The gas source 144 can be pressurized as desired to maintain gas within the gas source 144 and induce gas flow down gas-delivery lumen 142 when activated, such as by triggering gas flow with a valve or other actuator. In some cases, the operator can control the flow rate of the gas from the gas source 144 down the gas-delivery lumen 142, in other cases, the flow rate of the gas can be constant during application. The pressure of the gas from gas source 144 can be maintained as the gas is delivered down gas-delivery lumen 142. In some cases, gas flow can be triggered concurrently with first electrode 140 for generation of plasma, in other cases, gas flow can begin first before first electrode 140 is activated to ignite an arc and ionize the gas.

In general, this disclosure may use the terms "plasma," "conductive gas" and "ionized gas" interchangeably. A plasma includes of a state of matter in which electrons in a neutral gas are stripped or "ionized" from their molecules or atoms. Such plasmas can be formed by application of an electric field or by high temperatures. The first electrode 140 can induce ionization of a gas, for example, by application of a high temperature, up to about 45° C., so that the temperature is high enough to induce ionized of the gas to plasma, but not so high as to damage all tissue surrounding the first electrode 140. In a neutral gas, electrical conductivity can be non-existent or very low. Neutral gases act as a dielectric or insulator until the electric field reaches a breakdown value, freeing the electrons from the atoms in an avalanche process thus forming a plasma. Such a plasma provides mobile electrons and positive ions, and acts as a conductor which supports electric currents and can form spark or arc. Due to their lower mass, the electrons in a plasma accelerate more quickly in response to an electric field than the heavier positive ions, and hence carry the bulk of the current.

When the device 100 is in use for plasma generation, gas travels from the gas source 144 to the outlet of the gas-delivery lumen 142. There, the first electrode 140 produces enough energy to create an arc or spark between the gas and the treatment site. The energy can excite the gas molecules to a higher energy state. When the gas molecules fall back down from the excited energy state, ionization and dissociation can occur to the gas molecules, forming a plasma. Released plasma can penetrate the targeted treatment site tissue up to a few millimeters into the tissue, ablating or scarring the tissue and effectively treating endometriosis at shallower lesions. In other words, after excitation by the produced energy, the gas becomes an ionized gaseous substance that can be highly electrically conductive, also known as plasma. Plasma can include both high-temperature and low-temperature plasma, at both equilibrium and non-equilibrium states.

The specific wavelength of energy required to excite the gas and produce a plasma can depend on a variety of factors, including the type of gas selected, the distance from the outlet in the gas-delivery lumen 142 to the treatment site, and the density, pressure, or both, of the gas being delivered down gas-delivery lumen 142. The gas can flow from the gas source 144 out the gas-delivery lumen 142 at a rate specific to the type of gas chosen. In some cases, for example, where argon is used, the gas flow rate can be in the range of about 5 mL per second to about 50 mL per second, inclusive.

For the first electrode 140 configured to produce gas plasma, the device 100 can be connected to a radiofrequency (RF) or other wavelength source having a frequency of about 450 KHz to about 550 KHz, inclusive. For plasma generation, depending on the type of gas used, the device 100 can be connected to electrically power in the range of about 600 Vrms to about 1200 Vrms, and about 0.2 Amps to about 0.4 Amps, with an effective power of about 40 W to about 100 W. In general, the operator can situate the first electrode 140 so that it does not touch the treatment site, but is spaced apart so as to allow for ignition of an arc and creation of plasma. The operator can confirm the placement of the first electrode 140 with an optical camera or ultrasound as discussed above.

The delivery of electromagnetic energy via the first electrode 140 can turn gas into plasma between the treatment site and the first electrode 140, and can, in some cases, heat the tissue exposed to the plasma to above about 45° C. for a time interval appropriate to ablate the tissue at a depth of at least about 1 mm. In some cases, the device 100 can further include one or more thermal sensors on or near the distal portion 120 of the device so that the operator can verify a temperature range of the first electrode 140 during use. Ablation of the tissue at the treatment site can occur at up to about 3 mm to about 6 mm depth with this method. Ablation can occur rapidly, for example in about 60 seconds to about 120 seconds depending on the selected voltage at which the gas becomes electrically conductive. A number of other factors, including the pressure of the gas, the volume of internal area into which the shaft 110 portion of the device 100 is inserted, the flow rate or density of the gas through the lumen in shaft 110, the distance between the first electrode 140 and the treatment site, the voltage applied by first electrode 140, can be altered depending on the specific requirements of the operator and the patient.

In some cases, device 100 can be programmed to allow activation of first electrode 140 to produce plasma for a specific time period. For example, the source of electromagnetic energy to first electrode 140 can be programmed to run for an interval of about 60 seconds to about 120 seconds, as desired, to ablate endometrial tissue, and subsequently shut off. Scheduled time intervals can allow for ablation of endometrial tissue without damaging the myometrium.

Second electrode 150 can be an electromagnetic energy ablation electrode for ablation of deeper endometrial lesions than what may be treatable via exposure to a gas plasma treatment. Second electrode 150 can be located at or near a distal portion of shaft 110. Second electrode 150 can be actuatable (for example, by second trigger 164) to produce RF or another electromagnetic ablation energy. Prior to use, second electrode 150 can be triggered to slide longitudinally along shaft 110 towards a distal end of the distal portion 120 for electromagnetic ablation such that the second electrode 150 is no longer retracted.

Second electrode 150 can include, for example, a radiofrequency blade, spatula or other electromagnetic energy producing electrode for excising or ablating endometrial tissue. In some cases, second electrode 150 can be monopolar, in other cases, second electrode 150 can be bipolar in nature. If second electrode 150 is monopolar, a pad can be attached to the patient so that the second electrode 150 and the pad complete an electrical circuit. If the second electrode 150 is bipolar, the second electrode 150 can contain two portions that can complete the electrical circuit, for example, the second electrode 150 can include two prongs of a forceps. Second electrode 150 can, in some cases, be coupled to a source of electromagnetic energy, such as to electrosurgical energy generator circuitry.

Electromagnetic energy can include a variety of wavelengths of energy, including but not limited to, energy from sources such as radio frequency (RF) sources, and wavelengths of energy for excitation of gas particles to plasma. The second electrode 150 can, for example, produce and direct electromagnetic energy towards a treatment site such as for the purpose of tissue ablation without requiring plasma generation, for example, in the absence of gas delivery along the shaft 110.

The second electrode 150 can provide focused electromagnetic energy at a specific treatment site, for example, to a specific lesion of tissue. The direction of a focused amount of direct electromagnetic energy to a specific site can allow for deeper ablation at the treatment site.

The second electrode 150 can have a shape for physical excising of deep lesions of endometrial tissue. For example, second electrode 150 can include a retractable blade or spatula activated by electromagnetic energy, such that the operator can physically remove tissue at deep lesions. In cases where the second electrode 150 is in a blade or spatula configuration, retractability of the second electrode 150 can prevent patient harm during insertion of the device 100. If the operator is physically excising deep lesions of endometrial tissue with the second electrode 150, the operator can visualize the treatment site tissue with an optical device, such as a camera viewing tube used in laparoscopy, through ultrasound imaging, or endoscopically using an endoscope.

In general, the first electrode 140 can be used to apply a plasma over a more global treatment site, but at a shallower level. For example, where a large area of endometriosis occurs, the first electrode 140 can be used to spark plasma throughout that endometrial tissue, ablating the tissue at a depth of at least about 1 mm, and preferably about 3 mm to about 6 mm from the surface exposed within the uterus.

In contrast, the second electrode 150 can be used to apply electromagnetic ablation energy directly to a specific, localized treatment site at a deeper level. For example, if a particular pocket of endometrial tissue is a deep lesion, the second electrode 150 can be targeted to that lesion. To identify and treat deeper lesions, the operator can use visual aids to target these portions of tissue. Second electrode 150 can be used to ablate tissue extending to a depth below 6 mm from the surface exposed within the uterus.

When used in combination or alternatively, the first electrode 140 and the second electrode 150 can be used to treat more global and more local pockets of endometrial tissue, at varying depths. This can help allow for flexibility during the procedure depending on what the operator sees and what kind of endometriosis has built up in the patient. The flexibility to treat both locally and globally can help allow for a single invasive procedure to treat both shallow and deep lesions. For example, where the operator makes an incision near a treatment site containing endometriosis, the operator can treat both shallow, broader, lesions of endometriosis in and around the area of the incision, but can also treat deeper lesions, without removing the device 100 and inserting a second, different device with a different kind of electrode or tool to treat the second type of lesions. Instead, the operator can use the single device 100 to treat both types of lesions during one procedure, reducing overall time of operation, the number of incisions required in the patient, and the risk for error with multiple devices.

In some cases, the operator can treat a first set of shallow lesions with gas plasma, then visually identify a second set of deeper lesions to treat with RF ablation. Subsequently, the operator could identify a third set of lesions to treat. Depending on the nature of those lesions, the operator could treat them with plasma or RF ablation as desired. This is discussed more with regard to method 300 below.

FIG. 1A shows the device 100 in a plasma ablation mode using the first electrode 140 while FIG. 1B shows the device 100 in an electromagnetic ablation mode using the second electrode 150.

When the first electrode 140 is in used for plasma treatment, the second electrode 150 can be retracted towards proximal portion 130 of shaft 110. In some cases, second electrode 150 can be physically covered by a shield 152 when retracted. When activated, the shield 152 can physically separate the second electrode 150 from tissue and from the first electrode 140, such as to protect tissue from being cut by the second electrode during insertion. In some cases, the shield 152 an also electrically shield the second electrode 150 to prevent electromagnetic interference with the first electrode 140 when the device 100 is in plasma mode. The shield 152 can either be actuatable to move up over the second electrode 150 towards the distal portion 120 of the shaft 110, or the second electrode 150 can be actuatable to retract along the shaft 110 toward the proximal end 120 of the shaft 110. In the second case, the shield 152 can optionally be included closer the proximal end 120 to shield the second electrode 150 while retracted.

Retraction or shielding (or both) of the second electrode 150 can help allow for better user visibility when using first electrode 140 for plasma treatment, as the second electrode can be hidden from view of the operator when shielded. Retraction or shielding (or both) of second electrode 150 can be actuatable from first and second triggers 162, 164, on handle 160. Physical retraction of the second electrode 150 along the shaft 110, shielding of the second electrode 150 by the shield 152, or both, can be initiated automatically when the first trigger 162 activates plasma mode of the device 100. In other cases, physical retraction of the second electrode 150, shielding of the second electrode by the shield 152, or both, can be activated separately from various modes of the device 100, and either together or separate, by one or more triggers or buttons on or coupled to the handle 160.

When the device 100 is in electromagnetic ablation mode, and the second electrode 150 is in use, the second electrode 150 can be positioned near the distal portion 120, not retracted or shielded. In this position, the second electrode 150 can, in some cases, be positioned forward along the distal portion 120 so that it is further along the shaft 110 than the first electrode 140. The second electrode 150, shield 152, or both, can be positioned such that they physically shield the first electrode 140 from both use and view by the operator. In some cases, the second electrode 150 and the shield 152 can also electrically shield the first electrode 140 from use in this mode. This can allow for better visibility of the second electrode 150 and the treatment site by the operator. As discussed above, positioning of the second electrode 150 can be actuatable from the first and second triggers 162, 164, on the handle 160, or from other triggers, buttons, or actuatable features coupled to the handle 160.

Figure 2:
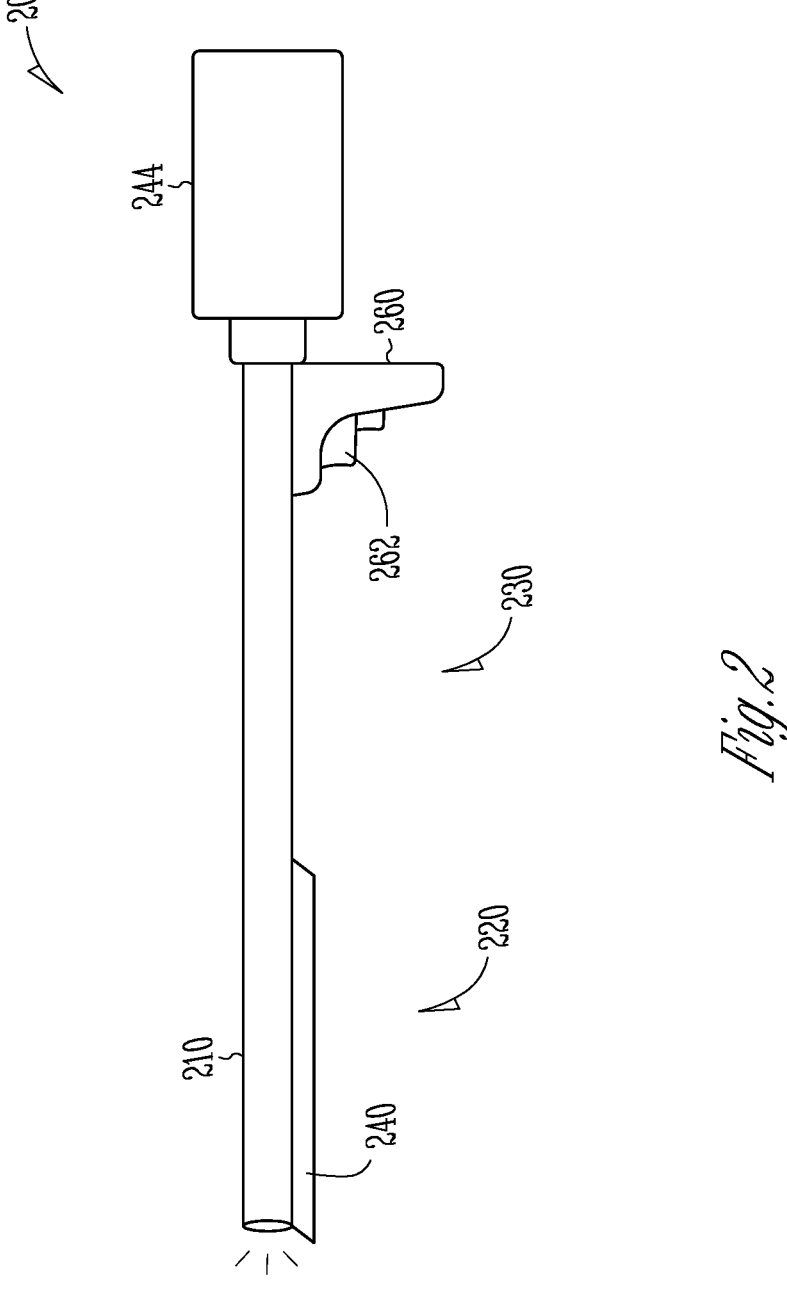
FIG. 2 illustrates a schematic diagram of an example of a device that can be used for treating endometriosis.

In some cases, the device 100 can be a self-contained device including the gas source 144, such as can include a canister within the handle. The device 100 can be electrically connected to an electrosurgical energy generator (ESG), which, in turn, can be plugged into an electricity source, or be battery operated. In some cases, the ESG and production of electricity can be actuatable from the handle 160 of the device, such as by the trigger 162, 164, or by other triggers, buttons, or actuatable features couple the handle 160. The device 100 can, in some cases, be a single-use device, where the whole device 100 is disposable after one use. The device 100 can be portable and easily moved. FIG. 2 is a schematic diagram illustrating an example of a portion of a device 200 for treating endometriosis. The device 200 can include, for example, an electrosurgical ablation system such as for treatment of endometriosis. The device 200 can include a shaft 210 with a distal portion 220 and a proximal portion 230, a single electrode 240 and a gas-delivery lumen 242 with a gas source 244 and a handle 260 with a trigger 262. The components of the device 200 can function similarly to the corresponding components of the device 100 as discussed with reference to FIGS. 1A-1B, except where otherwise noted.

The single electrode 240 can be actuatable for both generating plasma and for generating electromagnetic ablation energy. The single electrode 240 can have both a plasma mode and an electromagnetic ablation mode, which can be separately activated at various times. The single electrode 240 can include, for example, a monopolar or a bipolar electrode as discussed above with reference to the device 100.

In plasma mode, the operator can allow for a gas to flow from gas source 244 down the gas-delivery lumen 242 toward the distal portion 220 and out near the treatment site. The operator can then apply the appropriate electromagnetic energy and spark an arc between the treatment site and the single electrode 240, ionizing has therebetween and creating plasma to treat tissue at the treatment site, as discussed with reference to the first electrode 140 above.

In electromagnetic ablation mode, the operator can turn off gas flow from the gas source 244, and adjust the incoming electromagnetic energy as desired for the electromagnetic ablation treatment. The electromagnetic energy produced along the single electrode 240 can include both electromagnetic energy for ablation, such as RF energy, and electromagnetic energy at wavelengths appropriate for plasma generation. The plasma mode or the electromagnetic ablation mode can be selected as desired during treatment as the operator sees the needs of the patient during the procedure, such as through a camera tube or ultrasound imaging.

Figure 3:
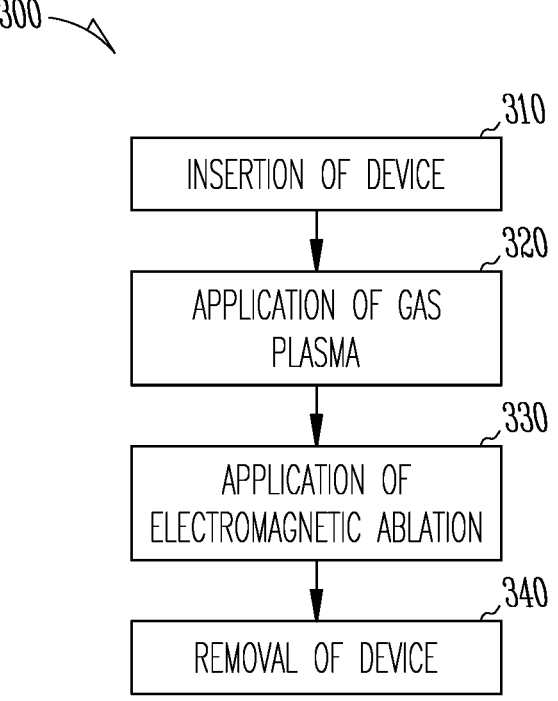
FIG. 3 illustrates a flow chart depicting an example of a method of treating a patient condition such as endometriosis.

FIG. 3 includes a flow chart illustrating an example of a method 300 of treating endometriosis with a device such as the device 100 or the device 200 discussed above. Method 300 can include providing the option for applying a gas plasma ablation treatment, an electromagnetic ablation treatment, or both, to a tissue treatment site in a patient.

First, for example in laparoscopy or open surgery, the operator can make an incision. The operator can insert a portion of the device into the patient, such as a distal portion of a shaft of the device. The operator can gently advance the shaft of the device until the distal portion is in place near the treatment site (step 310). Before insertion, the operator can optionally use an ultrasound visualization instrument to determine uterine and/or abdominal dimensions at the treatment site. When treating endometriosis, the treatment site may be outside the uterine cavity.

Steps 320 and 330, which include application of gas plasma ablation (step 320) and electromagnetic ablation (step 330), can be done in any order, and in some cases can each be repeated as desired by the operator.

For the application of gas plasma ablation, the operator of the device (e.g., device 100 or 200 discussed above) can first deliver a gas towards an in vivo treatment site of a patient (step 310). The operator can, for example, begin flow of gas by connecting the device to the gas source (e.g., a canister or line supplying the appropriate gas) and initiating flow of that gas down the 5 gas-delivery lumen of the device towards the treatment site. Initiation may occur by the operator pressing a trigger or button, or by opening or turning on the gas source.

The treatment site can include, for example, one or more endometriosis lesions in the abdomen such as within or near the uterine cavity, or elsewhere in the abdomen. The operator can induce the gas to travel from the gas source to the treatment site down a gas-delivery lumen in the device. The operator can manipulate the type of gas, pressure of the gas, and rate of gas flow through the device towards the treatment site, as desired for the particular patient. The gas can include, for example, one or more of carbon dioxide, argon, or other gas as appropriate. Once the gas flow reaches the end of the gas-delivery lumen, the gas can exit the lumen at the distal end of the shaft and disperse at or near the treatment site.

The operator can then generate plasma from the gas at or near the treatment site in vivo (step 320). The plasma can be generated by creating an arc between an electrode and the treatment site. The operator can induce this by providing appropriate electrical power and electromagnetic energy to interact with the dispersed gas, ionize that gas, and create a plasma on and near the treatment site. Using appropriate triggers, buttons, and/or other controls on the device, the operator can activate the electrode configured to generating plasma on the device near the inserted gas and by applying electromagnetic energy sufficient to ionize the gas at that particular location. The operator can manipulate the rate of plasma generation by altering the type of electromagnetic energy introduced, the electrode power output, the distance the electrode is from the treatment site, and other elements.

Sparking the arc and creating gas plasma can be done inside the patient, such as without requiring plasma build-up externally and at the entry point. In vivo generation of plasma near the treatment site can prevent plasma ablation or damage of tissue away from the desired treatment site, such as near the entry point for the device. For example, where argon is the gas of choice, radiofrequency energy can be applied in a range of about 450 KHz to about 550 KHz, and an effective power of about 40 W to about 100 W can be applied to ionize argon gas in vivo. The treatment site tissue can be directly exposed to the produced plasma, allowing for ablation up to about 6 mm. The exposure of the treatment site to plasma can continue for a period of up to about several minutes.

In some cases, a mixture or more than one type of gas may be used. In this case, the operator can particularly choose the type of gas desired based on the depth of endometriosis in the patient. The type of gas chosen can change the particular properties of the produced gas plasma. For example, some types of gas can create a gas plasma that will penetrate further into the tissue at the treatment site, while others will more broadly ablate the tissue but spread over a greater area. Depending on the particular patient needs, the operator can manipulate the types and amounts of gas used to generate plasma over one or more iterations.

For example, argon gas can be used as a first gas plasma treatment, and carbon dioxide gas can be used in a second sweep. Carbon dioxide gas generally creates plasma having wavelengths in the infrared (IR) range, which can ablate tissue differently than plasma having wavelengths in visual or ultraviolet (UV) ranges. IR range plasmas can cause more vibration in the tissue than other types of plasmas.

In some cases, selective excitation can be accomplished by manipulating the electromagnetic energy applied to the plasma activation electrode when generating the plasma from the gas. For example, where a specific wavelength of plasma is desired for treatment of a particular portion of tissue at the treatment site to a specific depth, an optical filter can be applied to the incoming plasma. The optical filter can, for example, be a medium that filters particular wavelengths of electromagnetic energy as they are incoming to the treatment site.

The ablation of tissue at the treatment site by the produce plasma(s) can also be affected by the tissue itself. For example, surface moisture of the tissue, or surface temperature of the tissue, can affect the amount or type of ablation created by the plasma. For example, surface moisture could be adjusted by irrigation from an additional or adjacent irrigation pathway including saline or water. The amount of moisture in the tissue could be monitored by a distal moisture sensor, and the operator could adjust the moisture as desired for the application of plasma, RF energy, or both. Likewise, surface temperature could be monitored by one or more distal temperature sensors, either included with the device or separate. Based on the sensed temperature, the operator could adjust the parameters for the first electrode, the second electrode, or both. For this reason, manipulation of gas plasma type and features can be helpful in tailoring a treatment plan specific to the patient and her endometriosis. In general, ablation by gas plasma can cause the endometrial tissue to be heated and scarred so that it does not continue to behave like a uterine lining outside of the uterus.

Once the operator has deemed the treatment site sufficiently treated with gas plasma such that necrosis has occurred at the treatment site, the operator can cease delivery of gas and production of plasma at that location. If needed, subsequently, additional around of gas plasma may be applied to the same treatment site, or to other treatment sites from the same entry point by the operator. Where particularly deep endometrial lesions have occurred, the operator may potentially use the same device for a focused electromagnetic ablation treatment.

For electromagnetic ablation treatment, the operator can stop or prevent delivery of gas to the treatment site, and instead activate an electrode with a specific frequency of electromagnetic energy to ablation particular lesions of tissue at the treatment site (step 330). The operator can apply this electromagnetic energy to lesions that are deep, and allow the direct application of RF or other electromagnetic energy to treat that tissue more deeply than the plasma (step 330). The electromagnetic ablation electrode can be either bipolar or monopolar.

In some cases, the electromagnetic ablation mode electrode can have a physical structure that is sized, shaped, arranged, or otherwise configured for cutting, such as a knife or spatula, such as to allow for physical manipulation with the produced electromagnetic energy. In this case, the operator can also excise certain lesions of tissue at the treatment site. This type of electromagnetic ablation can be useful where large geometries or "clumps" of endometrial tissue are found outside the uterine lining. Where a knife-type structure is used, electromagnetic energy can be used in conjunction with a cutting or slicing motion to remove endometrial lesions and ablate the remaining tissue to prevent the tissue from continuing to act like a uterine lining over the course of a monthly cycle outside of the uterine.

The operator can use the electromagnetic ablation electrode on one portion of tissue on or near the treatment site, or on multiple locations throughout a larger treatment area. If needed, the operator can treat one portion of tissue more than once as desired to ablate endometrial tissue.

Treatment with both the plasma activation electrode and the electromagnetic ablation electrode can induce necrosis in the treatment site tissue. This can scar the tissue, altering the tissue resistance after treatment. This treatment can prevent the tissue from continuing to act like the uterine lining outside the uterus, preventing endometriosis. The plasma treatment can be applied before, after, or in alternative to the electromagnetic energy ablation. The two treatment types can be each be applied more than once, to the same or differing areas of tissue within the treatment site.

For example, in one case, the general area can be first treated with plasma at a depth of up to about 6 mm. Then, specific deep lesions can be pin-pointed with electromagnetic ablation energy to excise those lesions at depths more than 6 mm. In an example, deep lesions can be pin-pointed and treated first with electromagnetic ablation energy. Subsequently, the plasma treatment can be used more globally. Each of these steps can be repeated as needed. The multiple treatment options here allows for operator flexibility in treating patients.

Once the operator has ablated the endometrial tissue, the operator can remove the device and, if appropriate, can proceed to close the entry point as needed (step 340).

ADDITIONAL EXAMPLES

Each of these non-limiting examples can stand on its own, or can be combined in various permutations or combinations with one or more of the other examples.

Example 1 can include an electrotherapeutic device for at least partial insertion into a patient, the device having: a shaft including a proximal portion and a distal portion, a gas-delivery lumen extending between the proximal portion and the distal portion of the shaft, and one or more electrodes located near the distal portion of the shaft. The one or more electrodes can include at least one plasma activation electrode configured to be actuatable for generating plasma from gas delivered to the distal portion of the shaft via the gas-delivery lumen, and the one or more electrodes can include at least one electromagnetic ablation electrode configured to be actuatable for generating electromagnetic ablation energy.

Example 2 can include Example 1, wherein the at least one electromagnetic ablation electrode is configured to be actuatable for generating electromagnetic ablation energy in the absence of gas delivery.

Example 3 can include any of Examples 1-2, wherein the at least one electromagnetic ablation electrode is configured to be user-retractable relative to the distal portion of the shaft.

Example 4 can include any of Examples 1-3, further including a shield configured to cover the at least one electromagnetic ablation electrode when the at least one electromagnetic ablation electrode is retracted.

Example 5 can include any of Examples 1-4, further including a gas source fluidly connected to the shaft to permit gas from the gas source to travel toward the at least one plasma activation electrode via the gas-delivery lumen.

Example 6 can include any of Examples 1-5, further including a handle connected to the shaft, the handle having a first trigger for receiving user input for actuating the plasma activation electrode, and a second trigger for receiving user-input for actuating the electromagnetic ablation electrode.

Example 7 can include any of Examples 1-6, wherein at least one electrode of the one or more electrodes is configured to be actuatable for both generating plasma and generating electromagnetic ablation energy.

Example 8 can include any of Examples 1-7, wherein the one or more electrodes comprise the at least one plasma activation electrode being separate from the at least one electromagnetic ablation electrode.

Example 9 can include any of Examples 1-8, wherein the at least one plasma activation electrode is configured to provide plasma to treat a patient more globally than the electromagnetic ablation energy provided by the electromagnetic ablation electrode.

Example 10 can include any of Examples 1-9, wherein the one or more electrodes are actuatable over a local treatment site.

Example 11 can include any of Examples 1-10, wherein the shaft comprises a width at the proximal portion, the width in a range of 1 mm to 5 mm, inclusive.

Example 12 can include a method of treating endometriosis including: delivering a gas toward an in vivo treatment site within a patient, generating plasma from the gas on or near the in vivo treatment site using a plasma activation electrode, exposing the treatment site to the plasma to treat endometrial tissue, and applying electromagnetic ablation energy to treat endometrial tissue.

Example 13 can include Example 12, wherein applying electromagnetic ablation energy to treat endometrial tissue comprises more deeply treating the tissue compared to treatment by the plasma.

Example 14 can include any of Examples 12-13, wherein applying electromagnetic ablation energy comprises excising endometrial tissue.

Example 15 can include any of Examples 12-14, wherein excising comprises using a knife electromagnetic ablation electrode or a spatula electromagnetic ablation electrode.

Example 16 can include any of Example 12-15, wherein generating plasma comprises striking an arc between the electrode and the gas by applying a power of about 40 W to about 100 W, inclusive.

Example 17 can include any of Examples 12-16, wherein the method includes applying electromagnetic ablation energy to a first treatment region, and exposing a larger-area second treatment region to the plasma.

Example 18 can include any of Examples 12-17, wherein the method includes applying electromagnetic ablation energy to a first treatment region, and focusing exposure by the plasma on the same first treatment region.

Example 19 can include any of Examples 12-18, wherein applying electromagnetic ablation energy to treat endometrial tissue is done before exposing the treatment site to the plasma.

Example 20 can include any of Examples 12-19, wherein exposing the treatment site to the plasma is done before applying electromagnetic ablation energy to treat endometrial tissue.

Example 21 can include an electrotherapeutic device for at least partial insertion into a patient, the device including: a shaft including a proximal portion and a distal portion, a gas-delivery lumen extending between the proximal portion and the distal portion of the shaft, and one or more electrodes located near the distal portion of the shaft. The one or more electrodes can be configured to be actuatable for establishing a plasma from gas delivered to the distal portion of the shaft via the gas-delivery lumen, and the one or more electrodes configured to be actuatable for generating electromagnetic ablation energy.

Example 22 can include Example 21, wherein the one or more electrodes are configured to generate AC electromagnetic ablation energy and to generate plasma from the gas.

Example 23 can include any of Examples 21-22, wherein the one or more electrodes comprise at least two plasma activation electrodes configured to produce plasma therebetween.

Example 24 can include any of Examples 21-23 wherein the at least two plasma activation electrodes are configured to each produce plasma.

Example 25 can include any of Examples 21-24 wherein the one or more electrodes comprise a plasma activation electrode at least partially surrounded in a housing having a plurality of pores for passage of at least one of gas or plasma therethrough.

Example 26 can include any of Examples 21-25 wherein the one or more electrodes comprise a first plurality of plasma activation electrode arranged in a first plane.

Example 27 can include any of Examples 21-26 further including a second plurality of plasma activation electrodes arranged in a second plane parallel to the first plane.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more," In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An electrotherapeutic device for at least partial insertion into a patient, the device comprising:
    a shaft including a proximal end portion and a distal end portion, the shaft defining a fluid-impervious gas-delivery lumen extending between the proximal end portion of the shaft, located at a handle connection, and the distal end portion of the shaft, the fluid-impervious gas-delivery lumen configured to deliver gas into the patient at the distal end portion of the shaft;
    a plasma activation electrode configured to be actuatable for generating plasma from the gas, the plasma activation electrode extending through the fluid-impervious gas-delivery lumen and extendable distally outward from the shaft via a distal opening at the distal end portion of the fluid-impervious gas-delivery lumen;
    an electromagnetic ablation electrode configured to be actuatable for generating electromagnetic ablation energy, the electromagnetic ablation electrode mounted in a fixed location on an external surface of the distal end portion of the shaft and offset from the plasma activation electrode; and
    a shield, both lateral to and outside of both of the shaft and the fluid-impervious gas-delivery lumen, the shield configured to be translated longitudinally and independently from the electromagnetic ablation electrode to selectively physically shield a distal tip of the electromagnetic ablation electrode from plasma generated by the plasma activation electrode when the plasma generation electrode is extended distally outward from the shaft.

2. The device of claim 1, wherein the electromagnetic ablation electrode is configured to be actuatable for generating electromagnetic ablation energy in an absence of gas delivery.

3. The device of claim 1, further comprising a gas source fluidly connected to the shaft to permit gas from the gas source to travel toward the plasma activation electrode via the fluid-impervious gas-delivery lumen.

4. The device of claim 1, wherein the plasma activation electrode is separate from the electromagnetic ablation electrode.

5. The device of claim 1, wherein the plasma activation electrode is configured to provide plasma to treat a patient more globally than the electromagnetic ablation energy provided by the electromagnetic ablation electrode.

6. The device of claim 1, wherein the electromagnetic ablation electrode is actuatable over a local treatment site.

7. The device of claim 1, wherein the shaft comprises a width at the proximal portion, the width in a range of 1 mm to 5 mm, inclusive.

8. The electrotherapeutic device of claim 1, wherein the shaft is sized and shaped for insertion to a uterus through a cervix.

9. The electrotherapeutic device of claim 1, further comprising a handle connected to the proximal end portion of the shaft, the handle comprising a first trigger for receiving user input for actuating the plasma activation electrode and a second trigger for receiving user-input for actuating the electromagnetic ablation electrode.

10. The electrotherapeutic device of claim 1, wherein the device is configured to be switched between a first mode where the plasma activation electrode is actuatable, and a second mode where the electromagnetic ablation electrode is actuatable.

11. An electrotherapeutic device for at least partial insertion into a patient, the device comprising:

a shaft including a proximal end portion and a distal end portion, the shaft defining a fluid-impervious gas-delivery lumen extending between the proximal end portion of the shaft, located at a handle connection, and the distal end portion of the shaft;

one or more plasma activation electrodes located near the distal end portion of the shaft, the one or more plasma activation electrodes configured to be actuatable for establishing a plasma from gas delivered to the distal end portion of the shaft via the fluid-impervious gas-delivery lumen an electromagnetic ablation electrode configured to be actuatable for generating electromagnetic ablation energy, the electromagnetic ablation electrode mounted in a fixed location on an external surface of the distal end portion of the shaft and offset from the plasma activation electrode;

a shield, both lateral to and outside of both of the shaft and the fluid-impervious gas-delivery lumen, the shield configured to be translated longitudinally and independently from the electromagnetic ablation electrode to selectively physically shield a distal tip of the electromagenetic ablation electrode from plasma generated by the plasma activation electrode when the plasma generation electrode is extended distally outward from the shaft; and a handle connected to the proximal end portion of the shaft, the handle comprising a first trigger for actuating the one or more plasma activation electrodes and a second trigger for actuating the one or more electromagnetic ablation electrodes.

12. The device of claim 11, wherein the electromagnetic ablation electrode is configured to generate AC electromagnetic ablation energy and the one or more plasma activation electrodes are configured to generate plasma from the gas.

13. The device of claim 12, wherein the at least two plasma activation electrodes are configured to each produce plasma.

14. The device of claim 11, wherein the one or more plasma activation electrodes comprise at least two plasma activation electrodes configured to produce plasma therebetween.

15. The device of claim 11, wherein the one or more plasma activation electrodes comprise a plasma activation electrode at least partially surrounded in a housing having a plurality of pores for passage of at least one of gas or plasma therethrough.

16. The device of claim 11, wherein the one or more plasma activation electrodes comprise a first plurality of plasma activation electrodes arranged in a first plane.

17. The device of claim 16, further comprising a second plurality of plasma activation electrodes arranged in a second plane parallel to the first plane.

\* \* \* \* \*